US00PP37093P2

(12) United States Plant Patent
NeSmith et al.

(10) Patent No.: US PP37,093 P2
(45) Date of Patent: Nov. 11, 2025

(54) BLUEBERRY PLANT NAMED 'CBG-23-01'

(50) Latin Name: *Vaccinium corymbosum*
Varietal Denomination: CBG-23-01

(71) Applicants: Rio Vista Farms Inc., Selma, CA (US); University of Georgia Research Foundation, Inc., Atens, GA (US)

(72) Inventors: D. Scott NeSmith, Griffin, GA (US); Gregory Willems, Kingsbury, CA (US)

(73) Assignees: Rio Vista Farms Inc., Selma, CA (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 18/884,792

(22) Filed: Sep. 13, 2024

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Karen M Redden
(74) *Attorney, Agent, or Firm* — Knobbe, Martens, Olson & Bear, LLP

(57) ABSTRACT

The new variety of blueberry 'CBG-23-01' is characterized by having fruit that ripens early in the season. The berries of 'CBG-23-01' have a sweet, aromatic flavor and mild acidity. Further, the berries of the new variety 'CBG-23-01' are crisp, with a smooth, firm texture.

10 Drawing Sheets

Latin name of the genus and species claimed: *Vaccinium corymbosum.*

Variety denomination: 'CBG-23-01'.

REFERENCE TO RELATED APPLICATIONS

This application is related to U.S. application Ser. No. 18/884,644, filed Sep. 13, 2024, U.S. application Ser. No. 18/884,736, filed Sep. 13, 2024, U.S. application Ser. No. 18/885,153, filed Sep. 13, 2024, and U.S. application Ser. No. 18/885,323, filed Sep. 13, 2024, which are directed to blueberry varieties developed by the same breeding program.

BACKGROUND AND SUMMARY OF THE INVENTION

Disclosed herein is a new and distinct southern highbush blueberry variety (*Vaccinium corymbosum*). The varietal denomination of the new variety is 'CBG-23-01'.

The new variety 'CBG-23-01' is a product of a hand-pollinated cross of seed parent 'TH-1492' (unpatented) and pollen parent 'TH-1870' (unpatented) made by D. Scott NeSmith in 2019 in Griffin, Georgia. The new variety 'CBG-23-01' was germinated from seed. The date of first planting of the new variety 'CBG-23-01' was November 2021. The new variety 'CBG-23-01' was selected by Gregory Willems in May 2023 in Reedley, California. Subsequent testing has demonstrated that the combination of traits disclosed herein that characterize the new variety are stable and retained true to type through successive generations of vegetative, asexual reproduction in Fresno County, California.

The new variety of blueberry 'CBG-23-01' is characterized by having fruit that ripens early in the season. The berries of 'CBG-23-01' have a sweet, aromatic flavor and mild acidity. Further, the berries of the new variety 'CBG-23-01' are crisp, with a smooth, firm texture. The new variety 'CBG-23-01' has not shown notable diseases or other pest problems beyond those also common for other blueberry varieties. The new variety 'CBG-23-01' has a chilling requirement of about 150-200 hours below 45° F.

The phenotype of the new blueberry variety 'CBG-23-01' may vary somewhat with variations in environment, such as temperature and light intensity, and cultural practices, without, however, any variance in genotype.

COMPARISON TO THE PARENTS

The new variety 'CBG-23-01' is distinguished from its seed parent 'TH-1492' (unpatented) in that the fruit of the new variety is firm, compared to a medium firmness for the fruit of 'TH-1492'. Further, the fruit of the new variety 'CBG-23-01' is sweeter and crunchier than the fruit of 'TH-1492'. Additionally, the fruit of the new variety 'CBG-23-01' ripens earlier, on about April 28$^{th}$ to April 30$^{th}$, compared to a mid-season ripening on about May 1$^{st}$ to 5$^{th}$ for the fruit of 'TH-1492'. Lastly, the new variety 'CBG-23-01' flowers around February 26$^{th}$, compared to about February 27$^{th}$ to March 3$^{rd}$ for 'TH-1492'.

The new variety 'CBG-23-01' is distinguished from its pollen parent 'TH-1870' (unpatented) by having large to very large sized fruit, compared to the medium to large sized fruit of 'TH-1870'. Additionally, the fruit of the new variety 'CBG-23-01' ripens later, on about April 28$^{th}$ to April 30$^{th}$, compared to about April 23$^{rd}$ to April 28$^{th}$ for 'TH-1870'. Lastly, the new variety 'CBG-23-01' flowers around February 26$^{th}$, compared to about February 20$^{th}$ to 23$^{rd}$ for 'TH-1870'.

COMPARISON TO CLOSEST VARIETY

The new variety 'CBG-23-01' resembles 'Suziblue' (U.S. Plant Pat. No. 21,167) and 'Emerald' (U.S. Plant Pat. No.

12,165) in that they are early season southern highbush blueberry cultivars with the same vigor. However, the new variety 'CBG-23-01' flowers and ripens on about February 26$^{th}$ and April 30$^{th}$, respectively, compared to about February 28$^{th}$ and May 7$^{th}$ for 'Suziblue' and February 15$^{th}$ and May 1$^{st}$ for 'Emerald' in Central California. Additionally, the new variety 'CBG-23-01' has larger sized berries than 'Suziblue' and 'Emerald'. Further the fruit of the new variety 'CBG-23-01' is softer than that of 'Emerald', but firmer than the fruit of 'Suziblue'.

TABLE 1

TABLE 1 shows a comparison of the characteristics of 'CBG-23-01', 'Suziblue' (PP21,167) and 'Emerald' (PP12,165). Rating scales are based on a score of 1 to 10, with 1 being the least desirable and 10 being the most desirable.

| | 'Suziblue' | 'Emerald' | 'CBG-23-01' |
|---|---|---|---|
| Berry Size | 8.0 | 8.0 | 9.1 |
| Berry Scar | 7.0 | 7.5 | 7.0 |
| Berry Color | 7.0 | 8.0 | 7.0 |
| Berry Firmness | 7.3 | 8.5 | 8.0 |
| Berry Flavor | 7.0 | 7.0 | 8.0 |
| Cropping | 8.5 | 8.5 | 7.5 |
| Plant Vigor | 8.0 | 8.0 | 8.0 |
| Date of 50% Flowering | Feb. 28 | Feb. 15 | Feb. 26 |
| Date of 50% Ripening | May 7 | May 1 | April 30 |
| Fruit Development Period | 69 days | 60 days | 65 days |

TABLE 2

TABLE 2 shows a comparison of the characteristics between the new variety 'CBG-23-01' and related varieties 'CBG-23-02', 'CBG-23-03', 'CBG-23-04' and 'CBG-23-05'.

| | 'CBG-23-01' | 'CBG-23-02' | 'CBG-23-03' | 'CBG-23-04' | 'CBG-23-05' |
|---|---|---|---|---|---|
| Season | Early | Early to mid-season | Early | Early to mid-season | Early to mid-season |
| Harvest date | April 18th-May 12th | April 28th-May 28th | April 18th-May 12th | May 3rd-June 1st | May 3rd-June 1st |
| Fruit size | Large, 20 mm-24 mm | Large, 19 mm-24 mm | Large, 18 mm-21 mm | Large, 18 mm-21 mm | Very large, 19 mm-22 mm |
| Flavor | Sweet, aromatic | Balanced sweetness and acidity | Balanced sweetness and acidity | Very sweet with mild acidity and floral undertones | Sweet with moderate acidity |
| Fruit Texture | Smooth, crisp | Crisp, firm | Crisp | Crisp | Smooth, crisp |
| Fruit Color | Deep blue | Medium blue | Light to medium blue | Medium blue | Medium blue |

BRIEF DESCRIPTION OF THE ILLUSTRATIONS

The accompanying color photographic illustrations taken in Reedley, California in 2024 pertain to 2.5 year old plants, and show the overall appearance and distinct characteristics of the new variety 'CBG-23-01'. The colors in the photographs are as true as possible and may differ slightly from the color values cited in the detailed botanical description, which accurately describes the colors of the new variety 'CBG-23-01'.

DESCRIPTION OF THE NEW VARIETY

Figure 1:
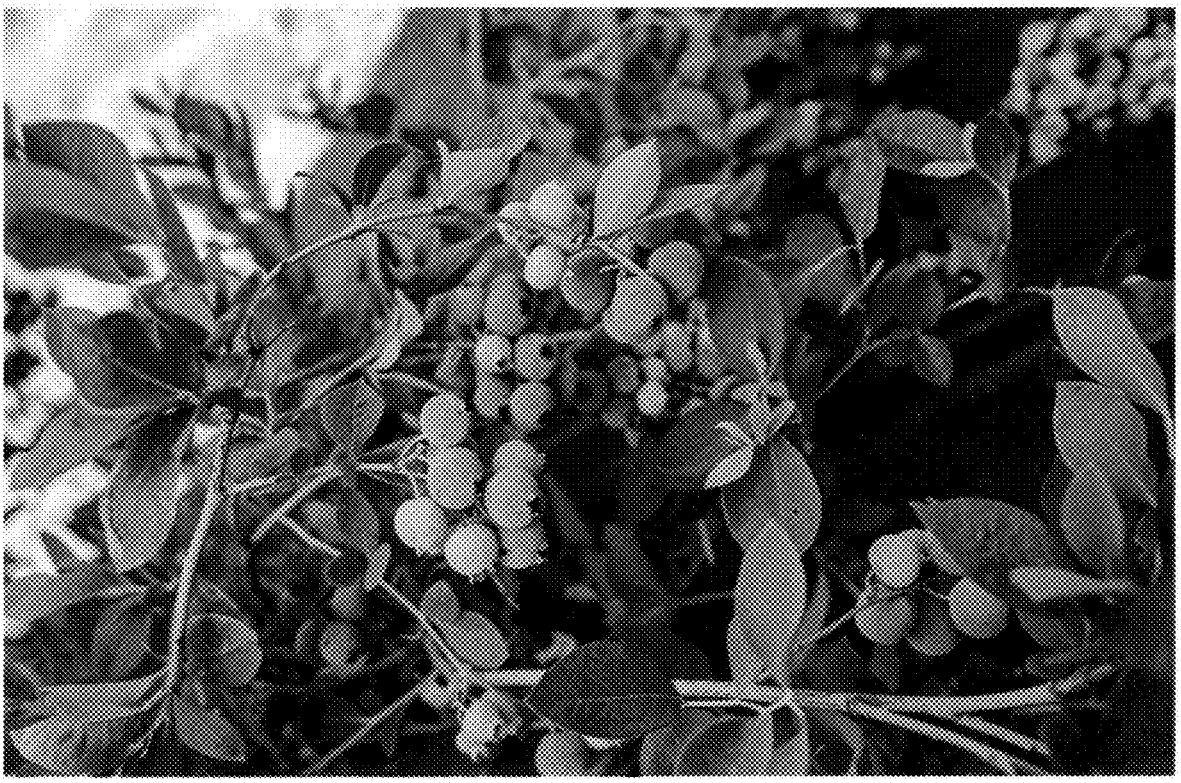
FIGS. 1-3 show the berries of the new variety 'CBG-23-01' on the plant ready for harvest.
Figure 2:
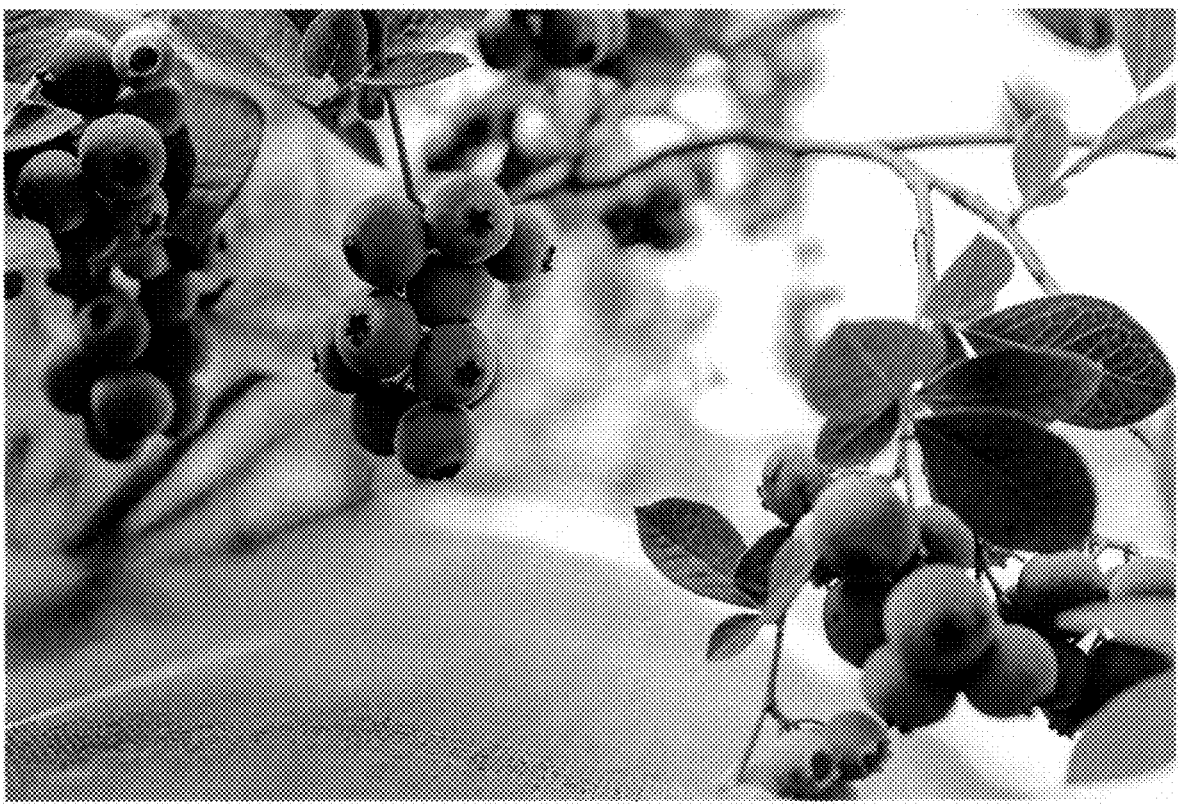
Figure 3:
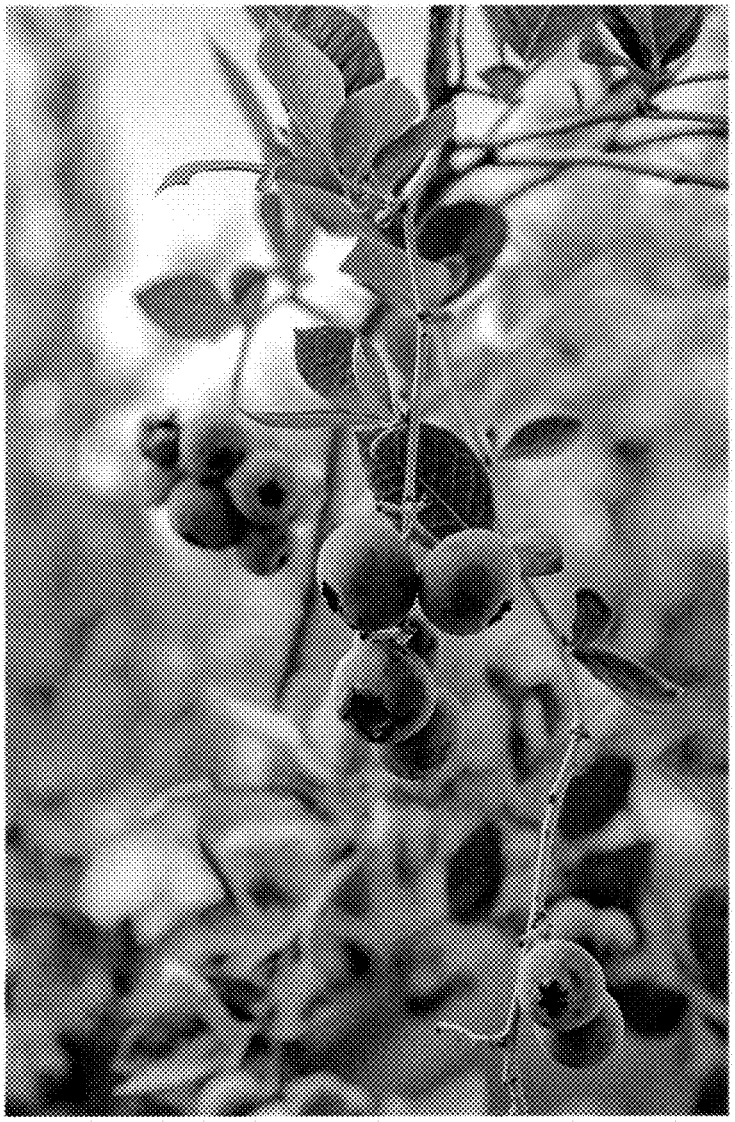
Figure 4:
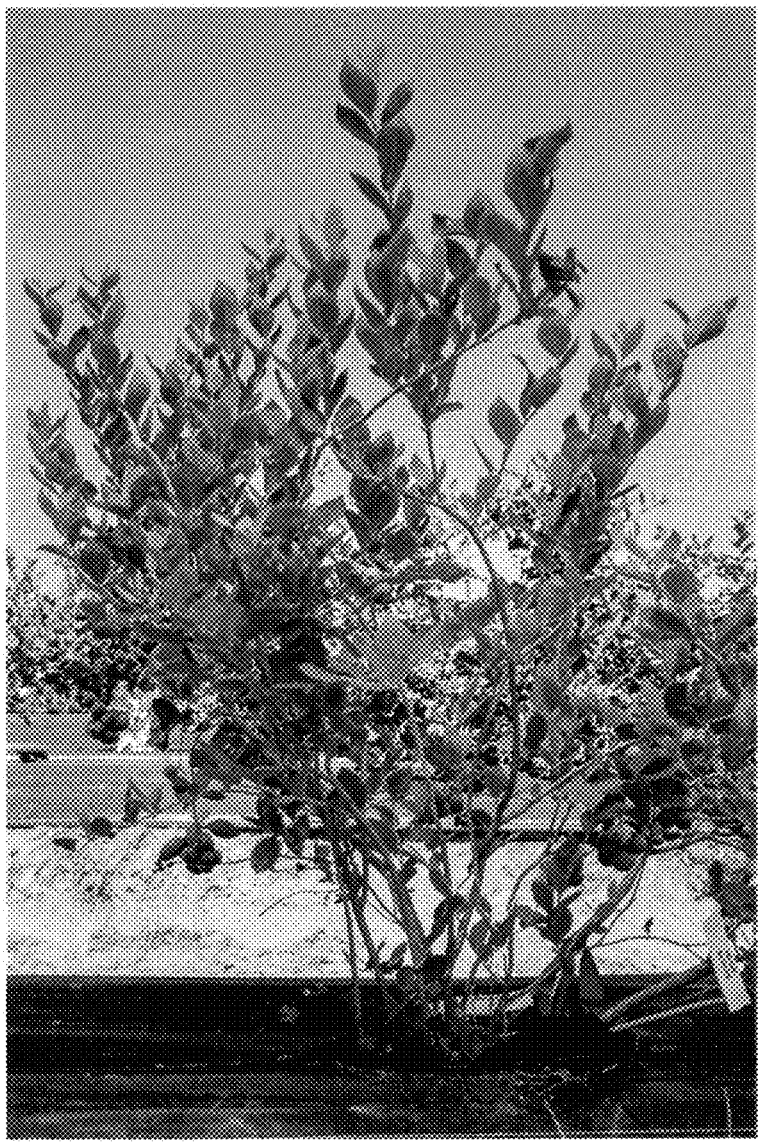
FIG. 4 shows the growth pattern of the plant of the new variety 'CBG-23-01'.
Figure 5:
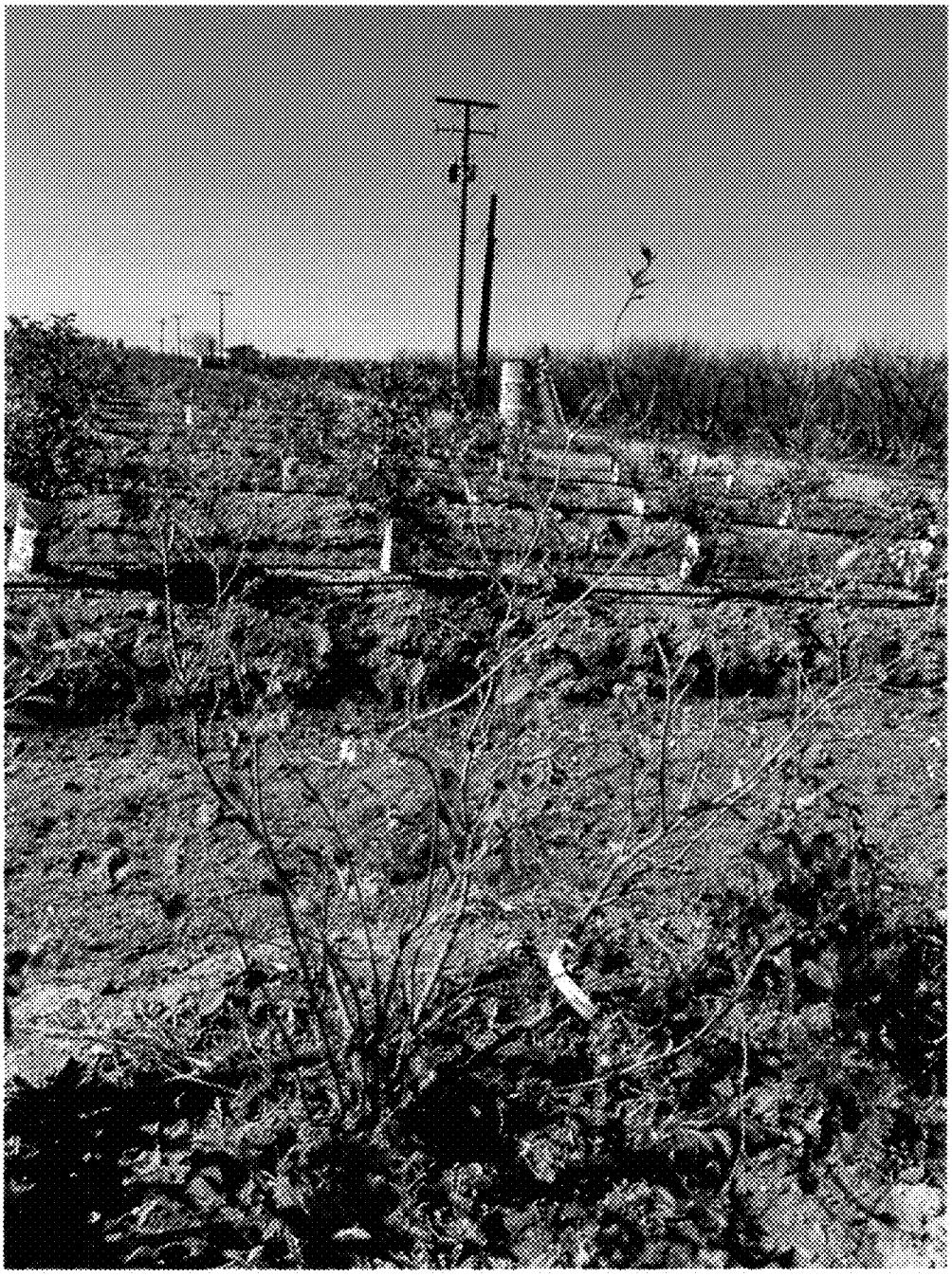
FIGS. 5 and 6 show the plant of the new variety 'CBG-23-01' during bloom.
Figure 6:
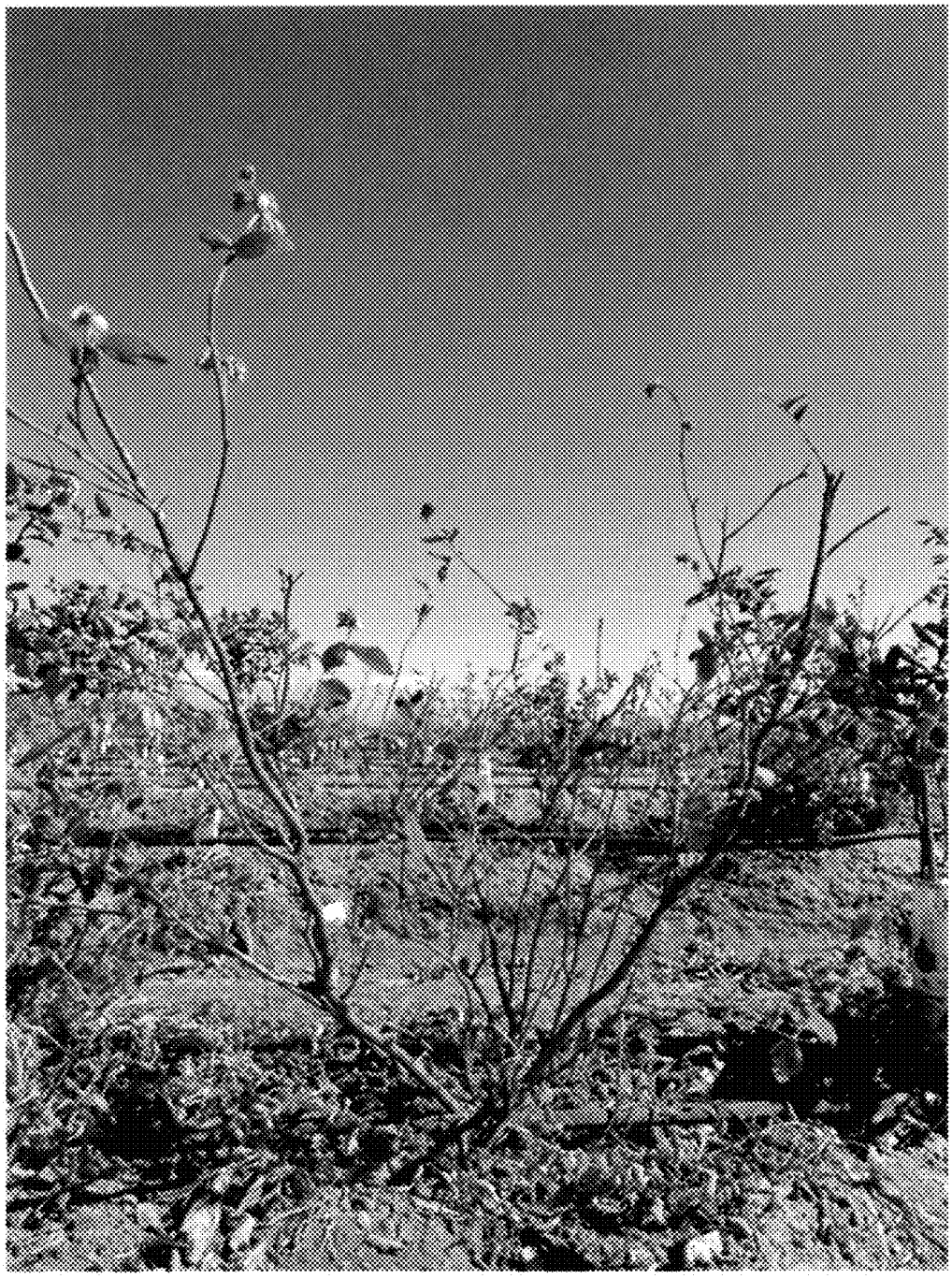
Figure 7:
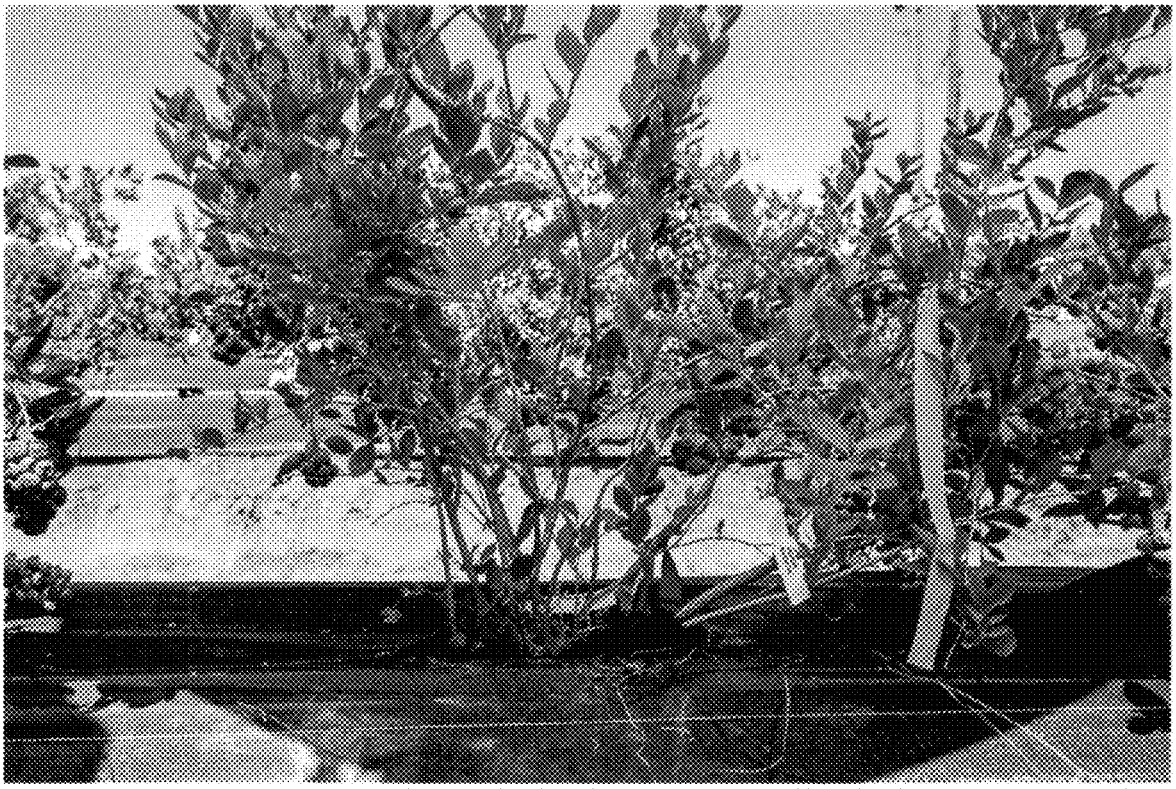
FIG. 7 shows the plant of the new variety 'CBG-23-01'.
Figure 8:
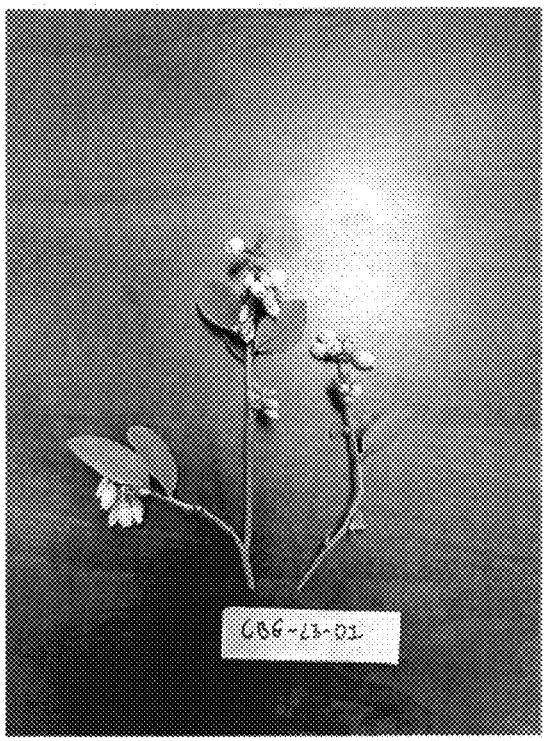
FIG. 8 shows the flowers of the new variety 'CBG-23-01'.
Figure 9:
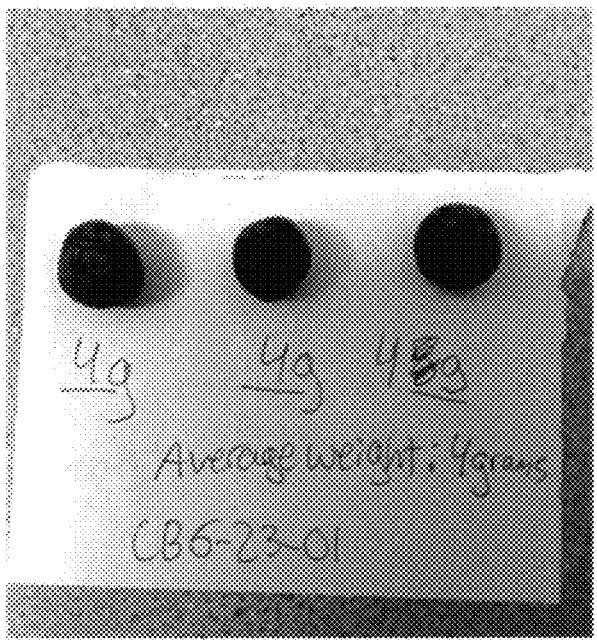
FIG. 9 shows the average berry weight of the new variety 'CBG-23-01'.
Figure 10:
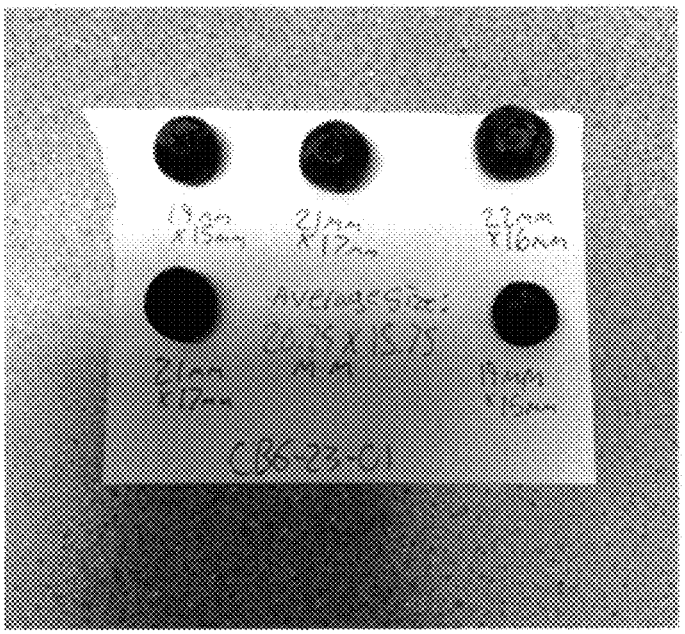
FIG. 10 shows the average berry size of the new variety 'CBG-23-01'.
Figure 11:
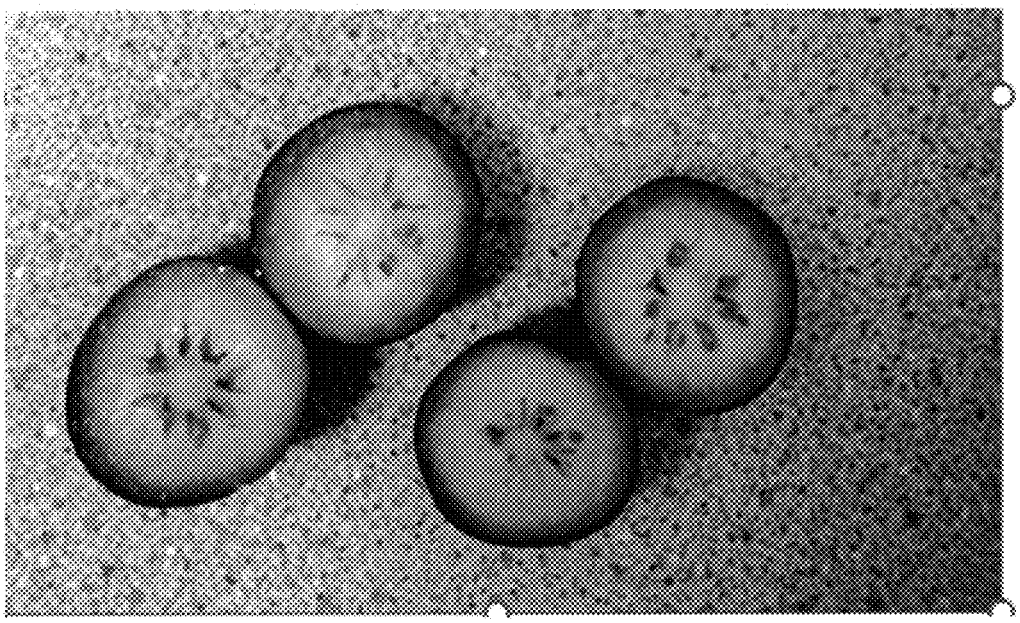
FIG. 11 shows the fruit of the new variety 'CBG-23-01' cut in half.
Figure 12:
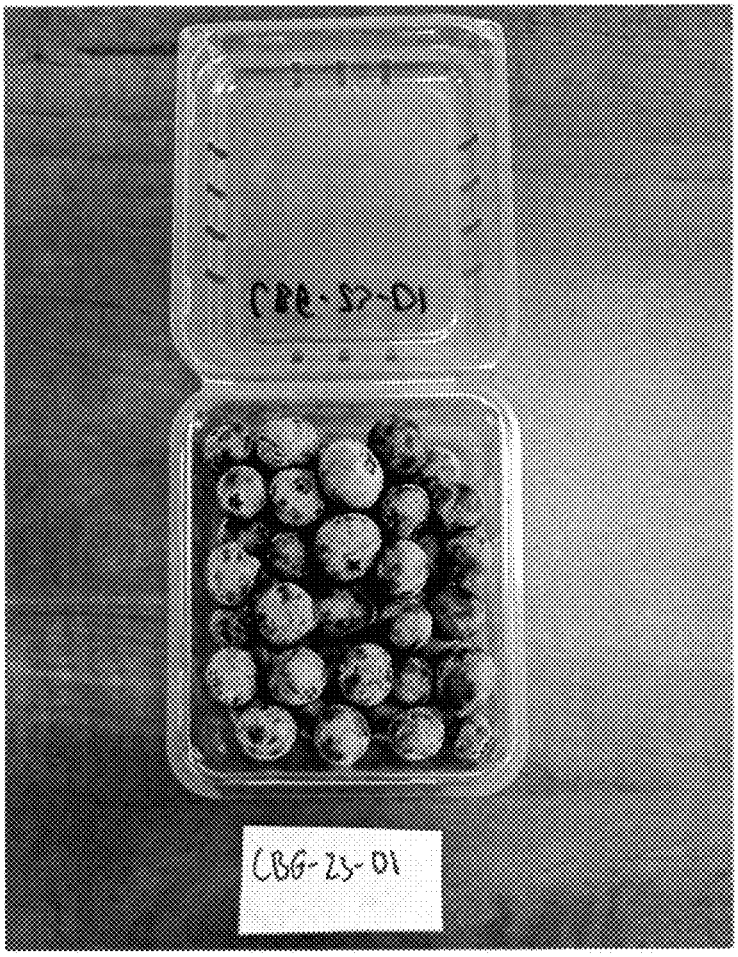
FIG. 12 shows the fruit of the new variety 'CBG-23-01' as a whole.

The following traits have been consistently observed in the original plant of the new variety 'CBG-23-01' and in asexually propagated progeny via vegetative cuttings in Fresno County, California. The descriptive matter which follows pertains to 2.5-year-old 'CBG-23-01' plants grown in the vicinity of Reedley, California during 2023, with supplemental irrigation, and is believed to apply to plants of the variety grown under similar conditions of soil and climate elsewhere. The dimensions, sizes, colors, and other characteristics given are to be understood to be approximations and averages set forth as accurately as practicable.

Throughout this specification, color names beginning with a small letter signify that the name of that color as used in common speech is aptly descriptive. Color names beginning with a capital letter designate values based upon The R.H.S. Colour Chart published by The Royal Horticultural Society, London, England, Sixth Edition, 2019 reprint. The colors and other phenotypic attributes may deviate from the stated values and descriptions depending upon variation in environmental, seasonal, climatic and cultural conditions.

General: The new variety 'CBG-23-01' produces fruit from about April 23$^{rd}$ to May 20$^{th}$. Measurements were taken on 2.5-year-old plants.

Plant:

*Root type.*—Fibrous.

*Growth rate.*—Moderately vigorous.

*Size.*—3.2 feet tall, 8-inch plant base/crown.

*Habit.*—Plants are dense with vertical growth and some spreading. It has 1-3 main canes with multiple branches within 15 cm of the surface of the soil.

*Productivity.*—About 2.3 pounds per plant.

*Cold hardiness.*—Similar to other early ripening southern highbush varieties.

*Chilling requirements.*—Approximately 150 to 200 hours of temperatures at or below 45° F. to induce normal leafing and flowering during the spring.

*Leafing.*—Plants readily break numerous leaf buds simultaneously with anthesis.

*Canes.*—Main Cane: Diameter: Approximately 14 mm. Color: About Medium Grey-Brown 199B. First Major Branch: Diameter: Approximately 5 mm. Color: About Medium Yellow-Green N144C. 2-year-Old Cane: Diameter: Approximately 13 mm. Color:

About Medium Grey-Brown 199B. Current Season Wood: Diameter: Approximately 4 mm. Color: About Medium Yellow-Green 144C.

*Fruiting wood*.—Numerous twigs approximately 15 to 25 cm in length and internode lengths of approximately 15 to 25 mm are common.

Foliage:

*Leaf color of mature leaves*.—Top side color: About Dark Green NN137A. Under side color: About Medium Green 138B.

*Leaf arrangement*.—Alternate simple.

*Leaf shape*.—Elliptic.

*Leaf venation*.—Pinnate with slight netting (or slightly reticulated).

*Leaf apices*.—Broadley acuminate.

*Leaf base*.—Cuneate to acute.

*Leaf length*.—Approximately 50 mm.

*Leaf width*.—Approximately 30 mm.

*Leaf margin*.—Crenate.

*Leaf surface*.—Glaucous (waxy).

*Petiole size*.—Small, approximately 3 mm long and 1 mm wide.

*Petiole color*.—About Light Yellow-Green145C.

*Petiole leaves margin*.—Smooth or ciliate; occasionally stalked with glands along the leaf margin.

Flower:

*Date of* 50% *anthesis*.—About February 26$^{th}$ in Central California.

*Flower shape*.—Urceolate.

*Flower bud number*.—High (6-10 buds per fruiting shoot).

*Flowers per cluster*.—Approximately 6-7.

*Flower fragrance*.—Yes.

*Corolla*.—Color: About Dark Green-White 157A for both the inner and outer surfaces. Length: About 8 to 9 mm. Width: About 6 to 7 mm. Aperture width: About 3 to 4 mm.

*Peduncle*.—Length: About 8 to 15 mm. Color: About Medium Yellow-Green 144A.

*Pedicel*.—Length: About 5 to 5.5 mm. Color: About Medium Yellow-Green 145B.

*Calyx*.—Calyx (with sepals) Diameter: Approximately 8 mm. Color center of calyx: About Medium Green 138B. Color of sepals: About Light Green 138C. Average sepals per calyx: About 5. Sepal length: Approximately 3 mm. Sepal width: Approximately 4 mm. Sepal color: About Medium Yellow-Green 144B. Sepal Texture: Slightly pubescent on the outer surface; smooth on the inner surface.

*Stamen*.—Length: About 5.5 to 7 mm. Number per flower: About 10. Filament color: About Medium Green-White 157B.

*Style*.—Length: About 8 to 9 mm. Color: About Medium Yellow-Green 145B.

*Pistil*.—Length: About 9 to 10 mm. Ovary color: About Medium Green 138B.

*Anther*.—Length: About 3.5 to 4 mm. Number: About 10. Color: About Medium Greyed-Orange 163A.

*Pollen*.—Abundance: Medium. Color: About Medium White NN155A. Self-compatibility: The cultivar has demonstrated a small degree of self-compatibility.

Fruit:

*Date of* 50% *maturity*.—About April 30$^{th}$.

*Fruit development period*.—About 65 days.

*Berry color*.—About Light Violet-Blue 98D with wax, and about Dark Black 203C without wax.

*Berry flesh color*.—About Medium Green 141D.

*Berry surface wax abundance*.—Medium.

*Berry weight*.—1$^{st}$ Harvest: Approximately 4 g. 2$^{nd}$ Harvest: Approximately 4 g.

*Berry size*.—Height from Calyx to Scar: Approximately 15.75 mm. Diameter: Approximately 20.25 mm.

*Berry shape*.—Spherical.

*Fruit stem scar*.—Small, dry and with no tears.

*Calyx*.—Approximately 3 mm deep and 6 mm wide.

*Sepals*.—Typically not visible; slightly turned inward and flat when present.

*Berry firmness*.—Firm, 8/10 on berry rating scale.

*Berry flavor*.—Sweet aromatic.

*Berry texture*.—Smooth, firm and crisp.

*Average brix*.—Approximately 13.20.

*Seed*.—Seed Abundance in Fruit: Medium. Seed Color: About Medium Greyed-Orange 165B. Seed Dry Weight: Approximately 34.2 mg per 100 seeds. Seed Size: Approximately 1.3 to 1.8 mm. Seed Quantity Average per Berry: About 19.

*Storage qualities*.—Shelf life of 'CBG-23-01' is moderate to long, maintaining quality under proper storage conditions. The berries were tested for storage longevity in a 39° F. (4° C.) refrigerated environment with low humidity for 21 days. The berries retained good texture, flavor, and firmness.

*Use/market*.—The berries of 'CBG-23-01' can be used as fresh fruit for shipping, customer-pick and processing markets. Not suitable for machine harvest.

*Disease resistance*.—Resistant to fungal diseases, but otherwise no noticeable disease resistance or susceptibility has been observed for 'CBG-23-01'.

We claim:

1. A new and distinct variety of blueberry plant named 'CBG-23-01' as illustrated and described herein.

* * * * *